United States Patent [19]
Kim et al.

[11] Patent Number: 5,584,072
[45] Date of Patent: Dec. 17, 1996

[54] HIP PROTECTOR

[75] Inventors: Bill H. Kim, 702 Doubletree La., Long Beach, Calif. 90815; Letitia C. Lau, Long Beach, Calif.

[73] Assignees: Bill H. Kim; Audrey H. Kim; Steven P. Lau; Letina C. Lau, all of Long Beach, Calif.

[21] Appl. No.: 512,975

[22] Filed: Aug. 9, 1995

[51] Int. Cl.$^6$ .................................................. A41D 13/00
[52] U.S. Cl. ............................................. 2/2; 2/22; 2/911
[58] Field of Search ............................. 2/22, 23, 2, 920, 2/908, 911, 919; 602/23

[56] References Cited

U.S. PATENT DOCUMENTS

| | | | |
|---|---|---|---|
| D. 201,861 | 8/1965 | Cummins | 2/22 X |
| 347,103 | 5/1894 | Berry. | |
| 522,967 | 7/1894 | Chapman et al. | |
| 835,219 | 11/1906 | Flick | 2/22 |
| 967,750 | 8/1910 | Fox | 2/22 |
| 1,088,273 | 2/1914 | Golden | 2/22 |
| 1,128,122 | 2/1915 | Fox | 2/22 |
| 1,229,947 | 6/1917 | Haggerty. | |
| 1,685,452 | 9/1928 | Goldsmith. | |
| 1,740,171 | 12/1929 | Goldsmith. | |
| 1,756,358 | 4/1930 | Ingram. | |
| 1,774,739 | 9/1930 | Voyne. | |
| 2,481,291 | 9/1949 | Coleman | 2/143 |
| 2,889,830 | 6/1959 | Raymond. | |
| 3,356,221 | 9/1970 | Garber. | |
| 3,801,984 | 4/1974 | Kanicki | 2/2 |
| 3,909,847 | 10/1975 | Holt et al. | 2/2 |
| 3,921,222 | 11/1975 | Hollman | 2/2 |
| 4,128,902 | 12/1978 | Siebert | 2/2 |
| 4,151,613 | 5/1979 | Rhee | 2/2 |

(List continued on next page.)

FOREIGN PATENT DOCUMENTS 2821906  11/1979  Germany ................................. 2/22

OTHER PUBLICATIONS

Lauritzen et al, "Effect of External Hip Protectors on Hip Fractures", *The Lancet*, vol. 341:Jan. 2, 1993 pp. 11–13.

Lauritzen et al, "Protection Against Hip Fractures by Energy Absorption", *Dan Med Bull*, Feb. 1992, vol. 39, No. 1, pp. 91–93.

Pierre J. Meunier, M. D., "Prevention of Hip Fractures", *The American Journal of Medicine*, Nov. 30, 1993, vol. 95 (suppl 5A), pp. 5A–75S–5A–78S.

Ross et al, "Evaluation of Two Interventions to Reduce Falls and Fall Injuries: The Challenge of Hip Pads and Individualized Elimination Rounds", *Managing Falls*, study supported by Grant #1–U01–NR0638 from the National Center for Nursing Research, NIH, pp. 97–103.

Wallace et al, "Iowa FICSIT Trial: The Feasibility of Elderly Wearing a Hip Joint Protective Garment to Reduce Hip Fractues", *JAGS*, Mar. 1993, vol. 41, No. 3 pp. 338–340.

*Primary Examiner*—Paul C. Lewis
*Attorney, Agent, or Firm*—Norman E. Brunell

[57] ABSTRACT

A hip protector using a matching pair of hip protector holsters interconnectable to form a waist encircling belt from which a pair of protective pad pockets are pivotally suspended over the patent's hips and secured in place by leg encircling straps. The hip protector is light weight and flexible for use under clothing and does not interfere with restroom activities. Each holster is identical and has a wide waist size adjustment range to minimize costs and inventory problems. The pads include impact absorbing base pads on which are positioned semi-rigid shells to distribute impact energy across the pad. The waist and leg encircling belts are secured by hook and loop fastening fabric for convenience and adjustability, and may be provided with an alternative hook and loop fastening fabric to service a substantially different range of leg sizes. The waist encircling belt may be locked with cable ties, a locking strap, or a locking buckle to ensure compliance. The locking belt prevents casual removal of the belt by patients that may not be counted on to continue compliance and may be used for the same purposes with other medical appliances.

37 Claims, 4 Drawing Sheets

U.S. PATENT DOCUMENTS

| | | | |
|---|---|---|---|
| 4,370,754 | 2/1983 | Donzis | 2/2 |
| 4,462,115 | 7/1984 | Carlson et al. | 2/2 |
| 4,472,839 | 9/1984 | Johansen | 2/2 |
| 4,573,216 | 3/1986 | Wortberg | 2/2 |
| 4,641,641 | 2/1987 | Strock . | |
| 4,674,157 | 6/1987 | Litz | 2/22 X |
| 4,688,558 | 8/1987 | Hooper, Jr. et al. | 2/908 X |
| 4,697,286 | 10/1987 | Cho | 2/22 |
| 4,709,692 | 12/1987 | Kirschengerg et al. | 2/908 X |
| 4,737,994 | 4/1988 | Galton | 2/2 |
| 4,761,834 | 8/1988 | Kolb | 2/2 |
| 4,807,301 | 2/1989 | Ferber | 2/2 |
| 4,991,230 | 2/1991 | Vacanti | 2/2 |
| 4,996,721 | 3/1991 | Beshro | 2/19 |
| 5,003,634 | 4/1991 | Brinkman | 2/46 |
| 5,011,334 | 4/1991 | Vorhauer | 2/911 X |
| 5,034,998 | 7/1991 | Kolsky | 2/2 |
| 5,086,514 | 2/1992 | Ross | 2/2 |
| 5,105,473 | 4/1992 | Valtakari | 2/22 X |
| 5,121,962 | 6/1992 | Weber et al. . | |
| 5,134,726 | 8/1992 | Ross | 2/23 |
| 5,157,789 | 10/1992 | Klass | 2/114 |
| 5,161,257 | 11/1992 | Arensdorf et al. | 2/2 |

HIP PROTECTOR

BACKGROUND OF THE INVENTION

1. Field of the Invention

The present invention relates generally to the field of medical devices and particularly to devices worn by patients, such as those worn for protection. In particular, the present invention relates to hip protectors worn by patients to reduce hip injuries, including devices worn by the elderly to reduce hip fractures, and other bone fractures in the pelvic area, resulting from falls.

2. Description of the Prior Art

Hip fractures are currently a significant cause of death and disability in the elderly. As people live to older ages, particularly in the more highly developed countries, the impact of hip fractures becomes even greater. Persons 80 years and older have mortality rates significantly higher, as much as eight times higher, than persons 60 years and younger.

Hip fractures are generally related to falls and osteoporosis, the later affecting on the order of one in four post-menopausal white women. As many as 90% of hip fractures occur due to a fall or other direct trauma to the hip.

Hip fractures, and other bone fractures in the pelvic area, are a major cause of morbidity and mortality in the elderly, currently costing billions of dollars in health care costs in the United States alone. Any significant reduction in the incidence or severity of hip injuries, particularly injuries in the elderly resulting from falls, would have a significant positive impact on society reducing the resultant morbidity, mortality and other social and economic costs.

Conventional devices for reducing the frequency and severity of hip and pelvic injuries fall into two general categories, sports related devices as well as devices for the elderly. Most such conventional devices are intended for selected care, that is, only worn by an individual with a particularly high risk of injury such as an athlete playing a high risk position in a particular sport, or an elderly person with significant osteoporosis. Other conventional devices target a wider market, such as a football pant modified with hip pads or hospital gowns with pads, to be worn by a wider group of people, e.g. all members of an athletic team or all high risk elderly patients in a hospital.

Attempts have been made over many years to design suitable hip and pelvic injury protectors, but conventional designs are usually bulky and cumbersome. Some conventional designs use adhesive materials to adhere protective pads directly to the skin which renders the devices both uncomfortable and impractical. Many conventional designs are relatively complicated, and use awkward devices such as air bladders. Such devices are often difficult for wide spread general use because they require many different sizes to be available. Such devices often hinder common actions, such as restroom activities.

One of the major problems to be solved with such devices is initial and ongoing placement of the protecting devices in the appropriate areas. Some hip protector devices use belts and other attachments to position protector pads, and keep them from riding up or otherwise changing position, while other such conventional devices are deficient in this area. In some conventional devices, such position controlling apparatus make it difficult for the user to properly put the medical device on or are uncomfortable for extended use. Similarly, with some users, the user's own activities such as lack of user compliance in properly operating the device and/or remembering to readjust the device after restroom activities make such conventional devices unsuitable for wide application.

One group of users having compliance problems with the ongoing continual use of medical devices that are worn about the body are the elderly, particularly those with Alzheimer's disease (or other forms of dementia). These patients are often the ones with the greatest need of assured compliance with the wearing and use of medical devices and are typically at greater risk of hip fractures. Unfortunately, it is difficult to assure their voluntary compliance with the use of any medical device or apparatus such as hip protectors. Indeed, such individuals often inappropriately remove their own clothing, pull out catheters, and are generally difficult management problems.

What are needed are relatively simple, easy to stock and use medical devices worn by the patients, such as hip protectors, that do not have the limitations of known devices, including those problems related to compliance.

SUMMARY OF THE INVENTION

The preceding and other shortcomings of the prior art are addressed and overcome by the present invention in which a medical device is worn about a portion of a patient's body.

In a first aspect, the present invention provides a hip protector which is configured from a pair of identical holster belts, each partially encircling the patient's waist. Each holster includes a pair of belt couplers, a pad pocket pivotally suspended from the belt, a protective pad positioned in the pocket, and a leg strap for encircling one of the patient's legs. In use, the pair of holsters are coupled to form a waist encircling belt, positioning each of the pad pockets on one of the patient's hips when each of the leg straps is secured about one of the patient's legs. A convenient locking device to assure compliance may be used with the hip protector so that it may be fastened to the patient to insure user compliance even with patients that do not normally voluntarily comply with the use of such devices.

In another aspect, the present invention provides a hip protector including a matching pair of hip protector holsters interconnectable to form a hip protector for a patient. Each of said holsters includes a holster belt for partially encircling said patient's waist, a pair of belt couplers, a pad pocket pivotally suspended from said belt, a protective pad positioned in said pocket, and a leg strap for encircling one of said patient's legs, whereby each of said belt couplers of one of said pair of holsters may be coupled to one of said belt couplers of the other of said pair of holsters to form a waist encircling belt positioning each of said pad pockets on one of said patient's hips when each of said leg straps is secured about one of said patient's legs.

In another aspect, the present invention provides a method of reducing hip and pelvic injuries in a large population of at risk patients by stocking a supply of identical hip protector holsters, positioning a protective pad in a pad pocket in each holster, interconnecting a pair of holsters to form a waist encircling hip protector for each at risk patient which positions one of protective pads at each of the patient's hips, and securing a leg strap for each holster to one of the patient's legs.

In another aspect, the present invention provides a device and method for assuring patient use compliance with a medical device by supplying a locking device to be secured by a care giver for preventing a patient from removing the medical device.

In still another aspect, the present invention provides a tamper resistant medical appliance, with a belt for encircling a portion of a patient's body, the belt being coupled to or part of the medical appliance, and a means for locking the belt such as a cable tie or tie wrap, for preventing a patient from casually removing the medical appliance.

These and other features and advantages of this invention will become further apparent from the detailed description and accompanying figures that follow. In the figures and description, numerals indicate the various features of the invention, like numerals referring to like features throughout both the drawings and the description.

DETAILED DESCRIPTION OF THE PREFERRED EMBODIMENT

Figure 1:
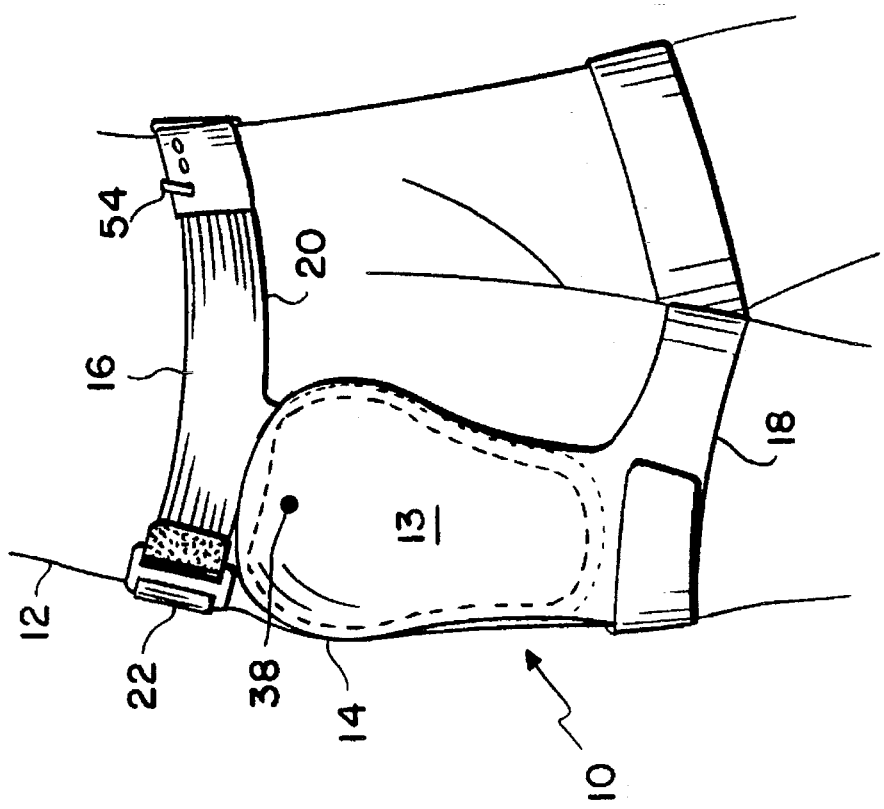
FIG. 1 is an isometric view of a hip protector according to the present invention worn by a patient shown in a partial front view.

The present invention provides a technique for positioning a pair of protective pads at the hips using an identical pair of holsters belted together to fit a patient. In particular, as shown in FIG. 1, hip protector 10 is worn on patient 12 so that pad pocket 13 of holster 14 is positioned on one of the patient's hips and held in place by the action of waist encircling belt 16 and leg strap 18 which encircles the patient's right leg as shown.

Figure 2:
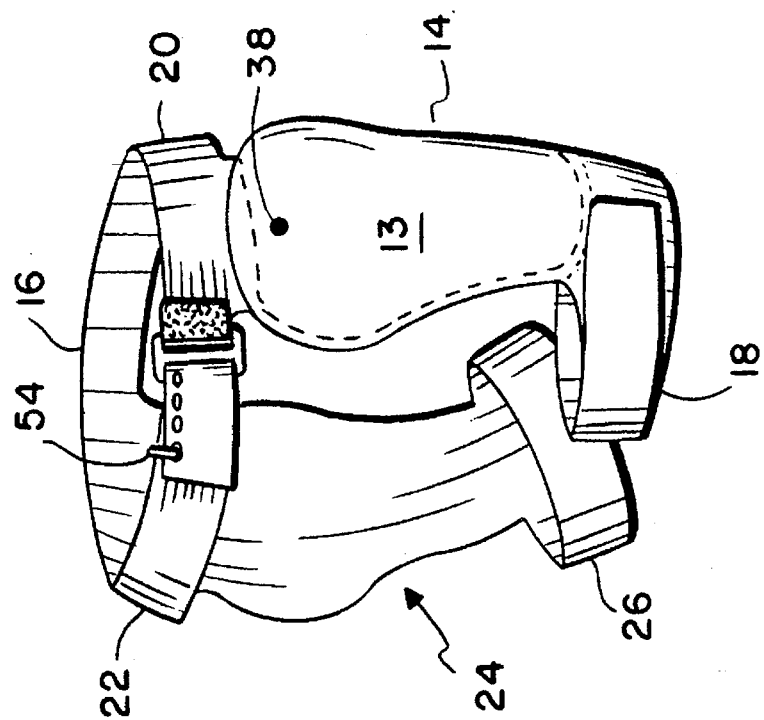
FIG. 2 is an isometric view of the hip protector of FIG. 1 shown in a partial rear view.

Waist encircling belt 16 is formed from the coupling of holster belt 20 of holster 14 and holster belt 22 of holster 24 which can be seen more clearly in FIG. 2. Holster 24 is secured to the right leg of patient 12 by leg strap 26. As will be described below in greater detail, the holsters are combinable with a substantial range of adjustment to fit the waist and leg sizes of a wide variety of patients.

Figure 3:
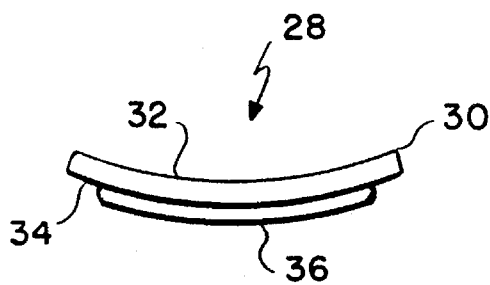
FIG. 3 is a top view of a protective pad used in the hip protector of FIG. 1.
Figure 4:
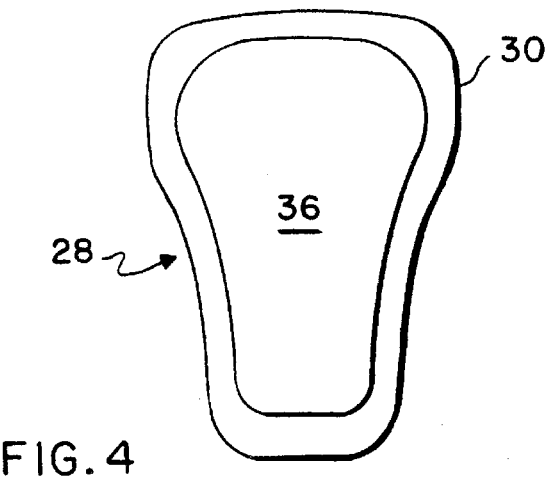
FIG. 4 is a front view of the protective pad of FIG. 3.

Referring now to FIGS. 3 and 4, protective pad 28 is constructed from at least two layers and formed to follow the contour of the patient's leg. Soft, flexible pad 30 which may conveniently be configured from a dense foam rubber or similar material, is pressed against the patient's leg on contact surface 32. On the opposite surface of flexible pad 30, surface 34, shell 36 is mounted. Shell 36 is formed of a more rigid material, such as a semi-rigid plastic or hard rubber, and serves to spread or distribute across flexible pad 30 any forces applied to any point on shell 36.

Figure 5:
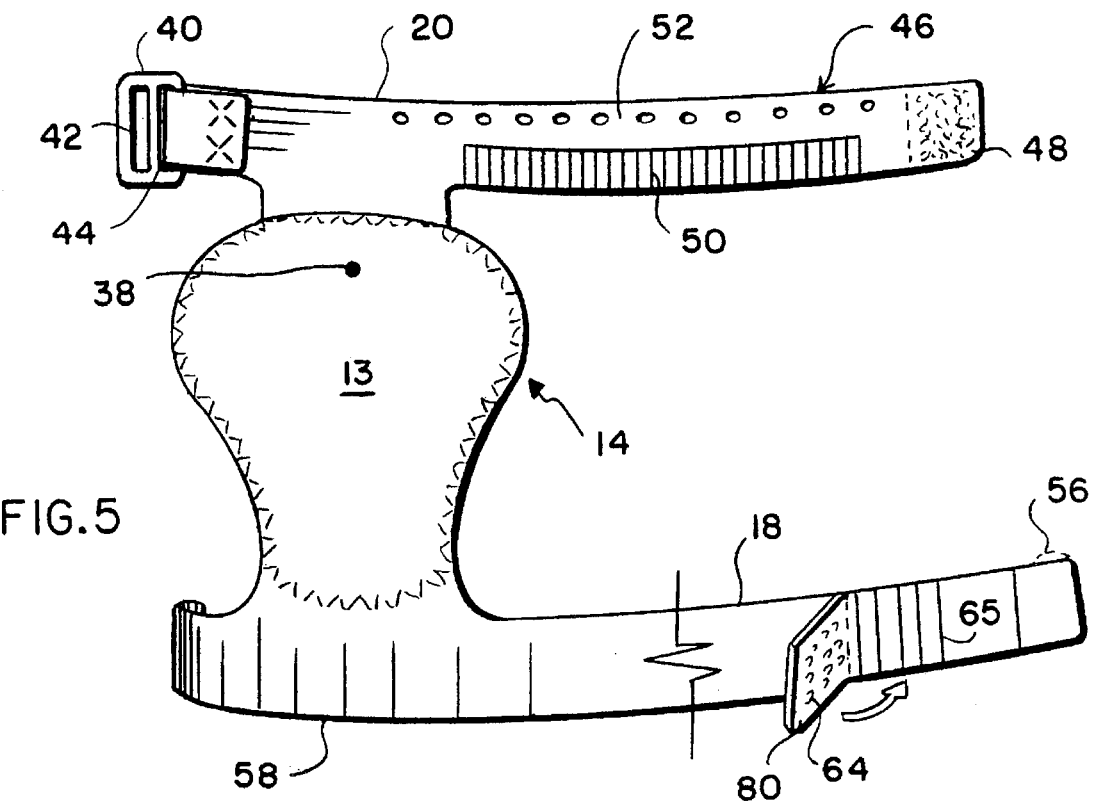
FIG. 5 is an isometric view of one of the pair of holster belts used in accordance with the present invention to form the hip protector of FIG. 1 including a bypass flap for gross adjustment of the diameter of the leg strap.

Referring now to FIG. 5, holster 14 is shown. Holsters 14 and 24 are identical and configured so that a pair of such holsters forms hip protector 10. Because the holsters are identical, only a series of identical holsters—rather than complete hip protectors—need be stocked in a large facility such as a hospital. For the same reason, a damaged holster may be replaced without replacing the entire holster. The fact that a pair of identical holsters are used therefore reduces the costs and difficulty of stocking supplies of such holsters.

Since the holsters are identical, only holster 14 need be shown or described in greater detail. Holster 14 includes protective pad 28, shown in FIGS. 3 and 4, positioned in pad pocket 13. Pad pocket 13 is pivotally supported by pivot 38 on holster belt 20 so that the patient may walk without disturbing the position of pad pocket 13, and therefore protective pad 28, on the patient's hips. Pad pocket 13 is secured to the patient's leg, so that hip protector 10 does not ride up on the patient, by leg strap 18.

Referring now to holster belt 20 in greater detail, one end of the belt includes belt intercoupler 40 in the nature of a belt buckle. In particular, as shown in FIG. 5, belt intercoupler 40 contains a pair of belt slots, 42 and 44, in a rigid body such as metal. The other end of holster belt 20 includes elongated belt tang 46.

When a pair of holsters, such as holsters 14 and 24 of FIGS. 1 and 2, are combined to form hip protector 10, the tang of holster belt 22 is inserted through belt slot 42 of belt intercoupler 40 and secured to itself. Similarly, belt tang 46 of holster belt 20 is inserted through the appropriate belt slot of holster belt 22 and fastened to itself to form waist encircling belt 16 of the appropriate size for the patient being fitted.

Belt tang 46 includes a pair of self fastening areas such as hook area 48 and loop area 50. As can been seen from FIG. 5, loop area 50 extends along a relatively long portion of holster belt 20 so that after insertion through the belt slot of holster belt 22, the length of holster belt 20 and therefore waist encircling belt 16 can easily be adjusted by fastening hook area 48 to a different portion of loop area 50.

In addition to hook area 48 and loop area 50, belt tang 46 includes a locking device such as hole row 52. After belt tang 46 is passed through the appropriate belt slot of holster 24 and hook area 48 is engaged with the portion of loop area 50 corresponding to the appropriate waist size for waist encircling belt 16, a simple, self-locking tie such as plastic cable tie 54 (shown in FIGS. 1 and 2) can be inserted through any mating holes in hole row 52 to lock waist encircling belt 16.

There are, however, some disadvantages to the use of hole row 52 to lock the waist encircling belt 16 in place using the plastic cable tie 54. In this configuration, plastic cable tie 54 must pass between the waist encircling belt 16 and the patient 12 as evident from an examination of FIG. 1. In many instances, this would result in potentially annoying contact between the cable tie and the patient's skin during securing and wearing of the device. Further, removal of the belt would typically entail cutting the plastic cable tie 54 next to the skin of the patient 12 which may both be annoying to the patient and would on occasion cause the patient to be cut slightly during removal.

Furthermore, creating a number of holes to form hole row 52 is expensive, and once done, it can be difficult for caregivers to align the holes for insertion of the plastic cable tie 54. An improved locking device is shown in detail below and described with regard to FIGS. 7 and 8.

Returning now to intercoupler 40 at the other end of holster belt 20 (as shown in FIG. 5), a portion of the belt is passed through belt slot 44 and permanently fastened to itself by, for example, rivetting or sewing. This permits belt slot 42 of intercoupler 40 to remain in the clear for use with the tang of holster 24.

Referring now in greater detail to leg strap 18, a similar self fastening arrangement is used in that hook area 56 is located at one end of leg strap 18 (on the side away from the viewer as shown) while a mating loop area 58 is positioned at the other end of leg strap 18 so that the strap may be comfortably fastened around the patient's leg and appropriately adjusted for size.

For smaller sized legs, a bypass flap 80 is provided which is used to effectively shorten leg strap 18. The bypass flap 80 includes an alternative hook area 64, which is similar to the hook area 56 at the end of the strap, but positioned only partway along the strap 18.

When bypass flap 80 is not in use, hook area 64 may conveniently be held out of the way, by for example fastening hook area 64 to loop area 65 which is positioned along leg strap 18 just beyond bypass flap 80. The strength of fastening between hook area 64 and loop area 65 need not be very great so that loop area 65 may be relatively small. In this way, as shown below in for example in FIG. 6, the end of leg strap 18 including loop area 58 also serves to protect the patient's skin from contact with either hook area 64 or loop area 65.

Figure 6:
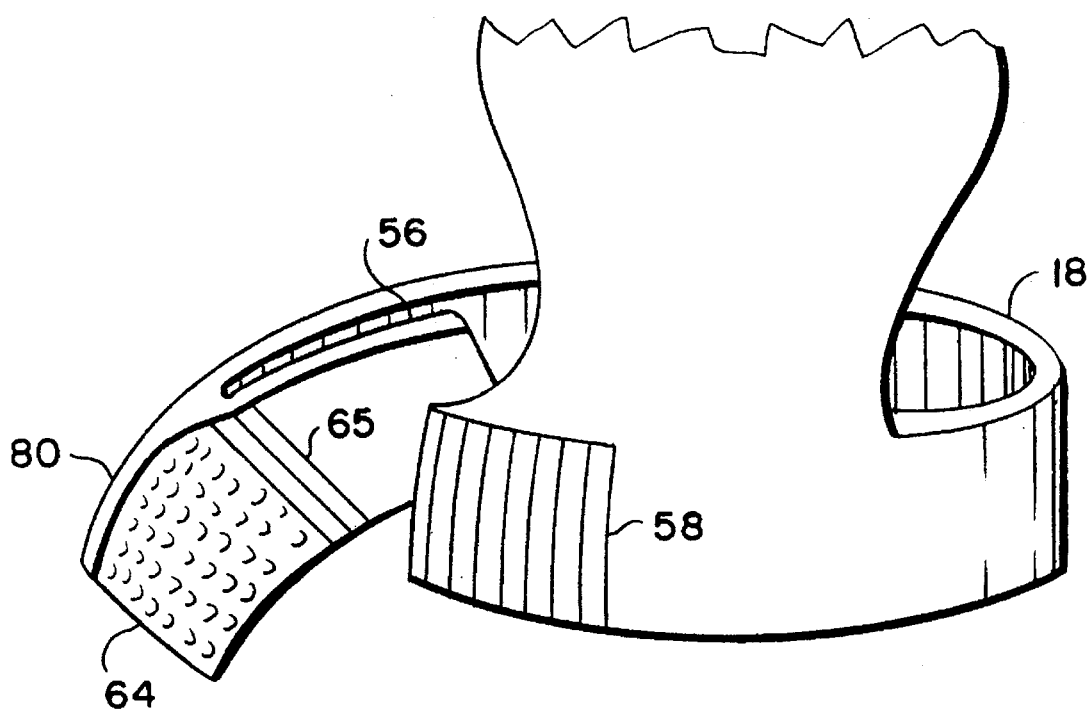
FIG. 6 is an isometric view of a lower portion of the holster belt shown in FIG. 5 in which the bypass flap is available for use for smaller diameter legs.

Referring now to FIG. 6, leg strap 18 is shown in a fastened and shortened state by means of bypass flap 80. In particular, the end of leg strap 18 including hook area 56 is folded back against the inner surface of leg strap 18 between the strap and the patient. Hook area 64 of leg strap 18 is used to fasten to loop area 58 to secure the strap around a smaller leg. Loop area 65 is prevented from contacting the patient's skin by the excess portion of loop area 58.

Figure 7:
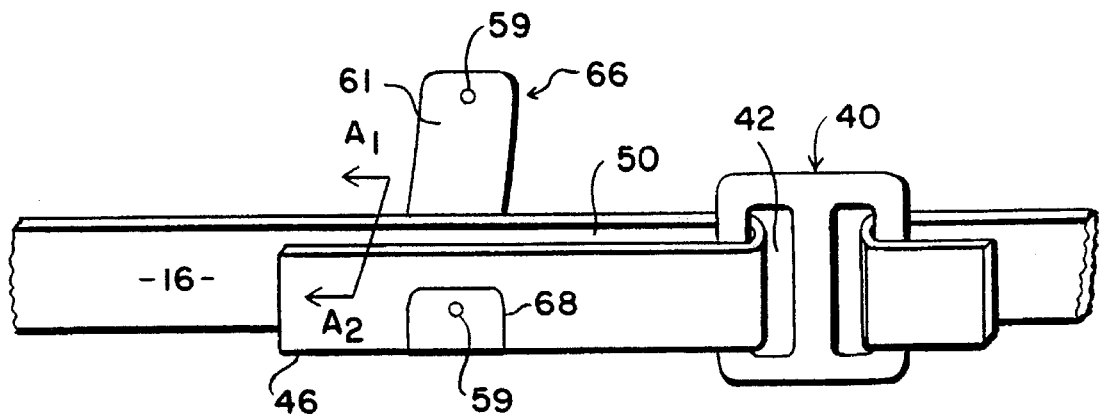
FIG. 7 is a isometric view of a front portion of a belt according to the present invention for encircling a body part, such as the waist, to hold a medical device in place with a locking strap.
Figure 8:
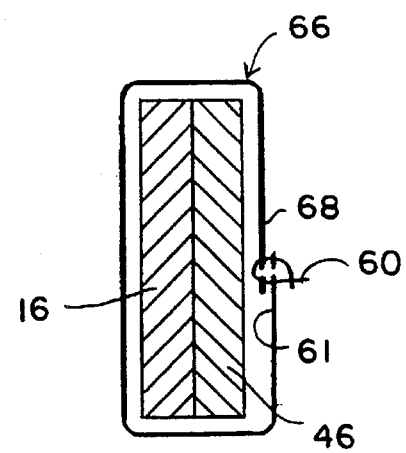
FIG. 8 is a cross sectional view along line $A_1$–$A_2$ of FIG. 7 in which the locking strap is shown in a locked position.

FIGS. 7 and 8 show an improved locking feature which may be used as an alternate to the use of hole row 52 and cable tie 54 of FIG. 5. This locking technique utilizes a locking strap 66, for preventing the casual or unintended removal of the hip protector 10 by for example an undisciplined patient. FIG. 8 shows a portion of the waist encircling belt 16 with the belt tang 46 inserted through the belt slot 42 and bent back upon itself so that the loop area 50 is in contact with the hook area 48 in accordance with the embodiment shown in FIG. 5.

The locking strap 66 has a hook side 61 which is pressed against the waist encircling belt 16, and a loop side 68, one portion of which is exposed as shown by folding the lower portion of locking strap 66 over belt tang 46. Both ends of locking strap 66 include a locking strap hole 59. Although only the portions of hook side 61 and loop side 68 of locking strap 66 surrounding locking strap hole 59 need to have hooks and loops, it is convenient to have the hooks and loops cover a substantial portion—if not all—of each such side. In use, the top portion of locking strap 66 is folded down tightly over waist encircling belt 16 to fasten with the lower portion thereof by engaging hook side 61 which loop side 68.

Referring now to FIG. 8, the locking strap holes 59 from each end of locking strap 66 may be aligned and secured together with any convenient tie, such as a self clinching cable tie 60 conventionally used to hold electrical wires in place. Cable tie 60 is used like the cable tie 54, shown in FIGS. 1 and 2, to lock the waist encircling belt 16 in place. The circumference of the cross section of waist encircling belt 16 shown in FIG. 8, formed by the belt tang 46 bent back and mated with itself, is slightly greater than the length of the locking strap 66 when locking strap holes 59 are aligned. In this way, locking strap 66 slightly compresses the portions of belt tang 46 when holes 59 are aligned and secured by cable tie 60. This compression resists movement of the portions of belt tang 46 relative to each other as well as movement of locking strap 66 along waist encircling belt 16.

The locking strap 66 is secured by passing the plastic cable tie 60 through both of the mated locking strap holes 59, passing it between the belt tang 46 and the locking strap 66, and securing it to itself. This securing process protects the patient because plastic cable tie 60 does not contact the patient's skin. Similarly, during use and subsequent removal, cable tie 60 rests against belt tang 46 which protects the patient's skin. In particular, cable tie 60 may conveniently be cut for removal without fear of damaging the skin.

Figure 9:
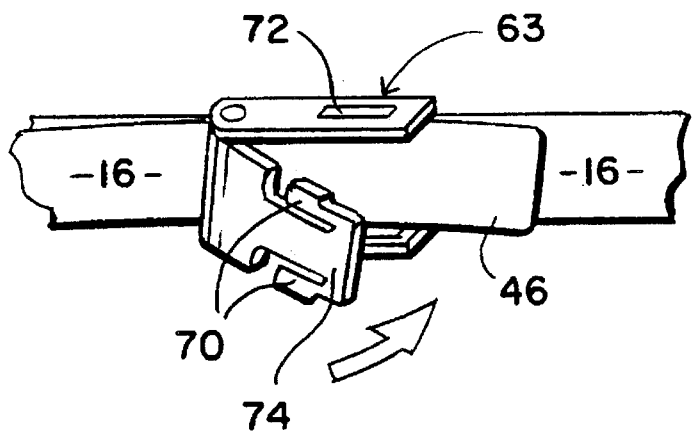
FIG. 9 is an isometric view of a front portion of the belt of the present invention showing an alternative embodiment including a buckle lock.

FIG. 9 shows buckle lock 63 used to lock the waist encircling belt 16 in place. The buckle lock 63 can be made from any number of materials, such as plastic or metal, and replaces the belt intercoupler 40 shown for example in FIG. 7. The buckle lock 63 will clamp the belt tang 46 in place using a pinching action, accomplished by pressure and friction of a closing lever 74 against the belt tang 46. The closing lever 74 has one or more locking springs, such as locking springs 70. When the buckle lock 63 is engaged, the closing lever 74 is pressed inward, toward the user's body. The closing lever is secured in place by the entrapment of each locking spring 70 within an aperture, such as aperture 72. In order to release the closing lever 74 and open the buckle lock 63, it is necessary to depress all locking springs 70 simultaneously. Such an action is relatively easy for a caregiver, yet difficult for patients with Alzheimer's disease or other forms of dementia, or who are otherwise mentally handicapped.

These are particularly convenient techniques for assuring compliance with the wearing of hip protector 10 for those patients, such as the very old or mentally incapacitated, for whom voluntary compliance may be a problem.

In operation, belt tang 46 of holster 14 is passed through the open belt slot on holster 24 and self fastened at the appropriate waist size by pressing hook area 48 against loop area 50. For units so equipped, the locking strap 66 is then wrapped around the section of the belt tang 46 in which it has been mated to itself by the loop area 50 being mated with the hook area 48 (FIG. 5). Similarly, after positioning hip protector 10 around the patient's waist, the tang of holster 24 is passed through belt slot 42 of intercoupler 40 and is likewise self fastened. If locking strap 66 is not used, a pair of disposable cable ties 54 may conveniently be passed through mating holes in hole row 52 of holster 14 and the equivalent holes in holster 24. If locking strap 66 is used, a disposable cable tie 60 may be inserted through the locking strap holes 59 in the locking strap 66, effectively locking hip protector 10 to the patient until removed by a nurse or other caregiver with scissors or similar cutting instruments. As noted above, units equipped with a buckle lock 63 can be secured by entrapping the locking springs 70 within the aperture 72, whereby the hip protector 10 is held in place until the locking springs 70 are released by the caregiver.

After belt 16 is secured, leg straps 18 and 26 may themselves be self-fastened about the patient's legs so that protective pads 28 are properly positioned about the patient's hips and maintained in that position as the patient moves around in a normal manner during the day or night. Depending upon the size of the users leg, the bypass flap 80 may be employed. It should be noted that hip protector 10 does not interfere with restroom activities and may be worn, without being noticeable, under normal clothing.

If the patient falls in a way that would injure the patient's hips, the forces of the fall or other injury strike shell 36 which distributes the forces across a large area of flexible pad 30 so that protective pad 28 substantially and effectively cushions the fall or other trauma greatly reducing injury to the patient. In many situations, such as a hospital, HMO (Health Maintenance Organization) facility or rest home environment, use of hip protector 10 by each and every patient will substantially reduce the number of disabling and life threatening hip injuries. The locking capability provided by hole row 52 and cable tie 54, or by the locking strap 66, or by the buckle lock 63, substantially improves compliance by those patients that would otherwise refuse to use, forget to use, or even otherwise remove hip protector 10.

Having now described the invention in accordance with the requirements of the patent statutes, those skilled in the art will have no difficulties making changes and modifications in the embodiment of the individual elements of the invention in order to meet their specific requirements or conditions. Such changes and modifications may be made without departing from the scope and spirit of the invention as set forth in the following claims.

What is claimed is:

1. A hip protector, comprising:

first and second matching hip protector holsters interconnectable by hand to form a hip protector for a patient, each of the holsters including:

a holster belt portion for partially encircling the patient's waist;

first and second belt couplers, the first belt coupler of the first holster being removably interconnectable by hand with the second belt coupler of the second holster and the second belt coupler of the first holster being removably interconnectable by hand with the first belt coupler of the second holster to interconnect the holster belt portions to form a holster belt for totally encircling the patient's waist;

a pad pocket pivotally suspended from the belt portion;

a protective pad positioned in the pocket; and a leg strap for encircling one of the patient's legs.

2. The invention of claim 1, wherein each of the protective pads further comprise:

an impact absorbing pad layer; and a semi-rigid shell layer centrally positioned on the impact absorbing pad layer for distributing impact energy, received by the shell layer, across the protective pad.

3. The invention of claim 1, wherein the first and second belt couplers of the first holster further comprises:

a belt loop fastened at one end of the holster belt portion of the first holster; and a belt tang at the other end of the holster belt portion of the first holster and adjustably connectable to a belt loop of the holster belt portion of the second holster.

4. The invention of claim 3, wherein the belt tang of the holster belt portion of the first holster further comprises:

an elongated portion of the holster belt portion of the first holster insertable through the belt loop of the holster belt portion of the second holster and fastenable thereto at various lengths to properly position each pad pocket for a variety of patient waist sizes.

5. The invention of claim 3, wherein the belt loop of the holster belt of the first holster further comprises:

an intercoupler having said one end of the holster belt of the first holster relatively permanently secured through a first belt slot in said intercoupler and a tang end of the holster belt of the second holster detachably secured through a second belt slot of said second holster.

6. The invention of claim 1, further comprising:

locking means associated with the first belt coupler of one holster and the second belt coupler of the other holster for locking said removably interconnectable couplers to each other to prevent casual removal of the hip protector by the patient by hand.

7. The invention of claim 6, wherein said locking means further comprises:

a plurality of apertures associated with said tang; and a self locking tie for securing a first and a second of said plurality of apertures together.

8. The invention of claim 3, further comprising:

a locking strap having a hook and loop fabric for securing said locking strap around said tang, said locking strap including a first and second plurality of apertures.

9. The invention of claim 8, wherein said locking strap further comprises:

a self locking tie for securing a first and a second of said plurality of apertures together.

10. The invention of claim 6, wherein said locking means comprises:

a buckle lock fastened to one end of the holster belt for grasping said tang, said buckle lock having at least one aperture; and a locking spring entrappable within the aperture to prevent casual removal of the hip protector by releasing said tang from said buckle lock.

11. The invention of claim 10, wherein said locking means further comprises:

a second locking spring entrappable within a second aperture to separately prevent casual removal of said hip protector by releasing said tang from said buckle lock, said buckle lock requiring both locking springs to be disentrapped from said apertures to permit removal of said hip protector.

12. The invention of claim 1 wherein the leg strap further comprises:

a leg encircling belt permanently fastened to a lower portion of the pad pocket;

a first portion of hook and loop fastening fabric on a first end of said leg encircling belt;

a first mating portion of said hook and loop fastening fabric on a first tang at a second end of said leg encircling belt for adjustably mating with said first portion of hook and loop fastening fabric a first range of leg sizes;

a second mating portion of said hook and loop fastening fabric on a second tang of said leg encircling belt, said second tang extending from said leg encircling belt intermediate said first end and said second end thereof, said second mating portion being fastenable to said first portion of said hook and loop fastening fabric, in lieu of said first mating portion, for adjustably fastening said leg encircling belt within a substantially different, second range of leg sizes.

13. The invention of claim 1 wherein the pad pocket further comprises:

an opening adjacent the waist encircling belt for removably inserting the protective pad in the pad pocket.

14. A method of reducing hip and pelvic injuries in at risk patients, comprising the steps of:

providing a supply of identical hip protector holsters;

positioning a removable protective pad in a pad pocket in each holster;

removably interconnecting a pair of identical holsters by hand to form a waist encircling hip protector for each at risk patient which positions one of the protective pads at each of the patient's hips; and securing a leg strap for each of the holsters to one of the patient's legs.

15. The invention of claim 14, wherein the step of positioning a protective pad further comprises the step of:

mounting a semi-rigid shell centrally on an impact absorbing layer to distribute impact energy across the protective pad.

16. The invention of claim 14, wherein the step of removably interconnecting the pair of hip holsters further comprises the step of:

removably fastening a belt tang of each hip holster through a belt loop of the other hip holster.

17. The invention of claim 16, wherein the step of fastening the belt tang further comprises the step of:

sizing the hip protector to fit the patient by adjusting the effective length the belt tang.

18. The invention of claim 17, wherein the step of interconnecting the pair of hip holsters further comprises the step of:

preventing casual removal of the hip protector by the patient without a cutting instrument.

19. The invention of claim 16, further comprises the additional step of:

locking each belt tang to itself through the belt loop of the other hip holster after the each such belt tang has been removably fastened to the corresponding belt loop.

20. The invention of claim 19, wherein the step of locking each belt tang to itself through the belt loop of the other hip holster further comprises the steps of:

wrapping a locking strap around the belt tangs and passing a locking tie through the locking straps.

21. The invention of claim 18, wherein the step of preventing casual removal of the hip protector by the patient further comprises the step of:

locking the waist encircling belt by closing a locking buckle.

22. The invention of claim 21, wherein the step of closing a locking buckle further comprises the step of:

securing locking springs within apertures in the locking buckle.

23. A tamper resistant medical appliance, comprising:

a medical appliance;

a belt for encircling a portion of a patient's body, said belt being coupled to said medical appliance;

a locking means for preventing casual removal of the medical appliance by an elderly patient by requiring removal of the belt by a care giver; and wherein the locking means comprises:

a first and a second plurality of apertures through said belt; and a self locking tie for securing said first and a second pluralities of apertures together.

24. The invention of claim 23, wherein said self locking tie further comprises:

a locking strap having a hook and loop fabric for securing said locking strap around said belt.

25. The invention of claim 24, wherein said locking strap further comprises:

a self locking tie for securing a first and a second of said plurality of apertures together.

26. The invention of claim 23, wherein said self locking tie further comprises:

a buckle lock fastened to one end of the belt for removably grasping the other end of said belt, said buckle lock having at least one aperture of said first and second pluralities of apertures; and a locking spring entrappable within the at least one aperture to prevent casual removal of the medical appliance by the elderly patient by requiring release of the locking spring from an aperture in said buckle lock by a caregiver.

27. The invention of claim 26, wherein said locking means further comprises:

a second locking spring entrappable within a second aperture to separately prevent casual removal of said medical appliance by releasing said belt from said buckle lock, said buckle lock requiring both locking springs to be disentrapped from said apertures to permit removal of said medical appliance.

28. A hip protector, comprising:

a matching pair of hip protector holsters interconnectable to form a hip protector for a patient, each of the holsters including:

a holster belt for partially encircling the patient's waist;

a pair of belt couplers;

a pad pocket pivotally suspended from the belt;

a protective pad positioned in the pocket; and a leg strap for encircling one of the patient's legs, whereby each of the belt couplers of one of the pair of holsters may be coupled to one of the belt couplers of the other of the pair of holsters to form a waist encircling belt positioning each of the pad pockets on one of the patient's hips when each of the leg straps is secured about one of the patient's legs, wherein the pair of belt couplers includes a belt loop securely fastened at one end of the holster belt; and a belt tang adjustably connectable to the belt loop of the other holster; each of the belt tangs including means for fastening an end portion of the tang to a mid portion of the tang to adjust the length of the resultant waist encircling belt; and locking means for securing the end portion to the mid portion of the tang to prevent casual removal of the hip protector by the patient; said locking means including a plurality of apertures associated with said tang; and a self locking tie for securing a first and a second of said plurality of apertures together.

29. The invention of claim 28, further comprising:

a locking strap having a hook and loop fabric for securing said locking strap around said tang, said locking strap including said first and second of said plurality of apertures.

30. A hip protector, comprising:

a matching pair of hip protector holsters interconnectable to form a hip protector for a patient, each of the holsters including:

a holster belt for partially encircling the patient's waist;

a pair of belt couplers;

a pad pocket pivotally suspended from the belt;

a protective pad positioned in the pocket; and a leg strap for encircling one of the patient's legs, whereby each of the belt couplers of one of the pair of holsters may be coupled to one of the belt couplers of the other of the pair of holsters to form a waist encircling belt positioning each of the pad pockets on one of the patient's hips when each of the leg straps is secured about one of the patient's legs, wherein the pair of belt couplers includes a belt loop securely fastened at one end of the holster belt; and a belt tang adjustably connectable to the belt loop of the other holster; each of the belt tangs including means for fastening an end portion of the tang to a mid portion of the tang to adjust the length of the resultant waist encircling belt; and locking means for securing the end portion to the mid portion of the tang to prevent casual removal of the hip protector by the patient; said locking means including a buckle lock fastened to one end of the holster belt for grasping said tang, said buckle lock having at least one aperture; and a locking spring entrappable within the aperture to prevent casual removal of the hip protector by releasing said tang from said buckle lock.

31. The invention of claim 30, wherein said locking means further comprises:

a second locking spring entrappable within a second aperture to separately prevent casual removal of said hip protector by releasing said tang from said buckle lock, said buckle lock requiring both locking springs to be disentrapped from said apertures to permit removal of said hip protector.

32. A method of reducing hip and pelvic injuries in a large population of at risk patients, comprising the steps of:

providing a supply of identical hip protector holsters;

positioning a protective pad in a pad pocket in each holster;

interconnecting a pair of holsters to form a waist encircling hip protector for each at risk patient which positions one of the protective pads at each of the patient's hips; and securing a leg strap for each of the holsters to one of the patient's legs; the step of interconnecting the pair of hip holsters further including fastening a belt tang of each hip holster through a belt loop of the other hip holster; including sizing the hip protector to fit the patient by adjusting the effective length of the belt tang; the step of interconnecting the pair of hip holsters including preventing casual removal of the hip protector by the patient; including locking each belt tang to itself through the belt loop of the other hip holster; and wrapping a locking strap around the belt tangs and passing a locking tie through the locking straps.

33. A method of reducing hip and pelvic injuries in a large population of at risk patients, comprising the steps of:

providing a supply of identical hip protector holsters;

positioning a protective pad in a pad pocket in each holster;

interconnecting a pair of holsters to form a waist encircling hip protector for each at risk patient which positions one of the protective pads at each of the patient's hips; and securing a leg strap for each of the holsters to one of the patient's legs; the step of interconnecting the pair of hip holsters further including fastening a belt tang of each hip holster through a belt loop of the other hip holster; including sizing the hip protector to fit the patient by adjusting the effective length the belt tang; the step of interconnecting the pair of hip holsters including preventing casual removal of the hip protector by the patient; including locking the waist encircling belt by closing a locking buckle.

34. The invention of claim 33, wherein the step of closing a locking buckle further comprises the step of:

securing locking springs within apertures in the locking buckle.

35. A tamper resistant medical appliance, comprising:

a medical appliance;

a belt for encircling a portion of a patient's body, said belt being coupled to said medical appliance; and a locking means for said belt, for preventing casual removal of the medical appliance by the patient, including a plurality of apertures associated with said belt; and a self locking tie for securing a first and a second of said plurality of apertures together.

36. The invention of claim 35, further comprising:

a locking strap having a hook and loop fabric for securing said locking strap around said belt, said locking strap including said first and second of said plurality of apertures.

37. The invention of claim 35, wherein said locking strap further comprises:

a self locking tie for securing a first and a second of said plurality of apertures together.

* * * * *